(12) United States Patent
Wu et al.

(10) Patent No.: US 12,191,449 B2
(45) Date of Patent: Jan. 7, 2025

(54) SECONDARY BATTERY AND DEVICE COMPRISING THE SAME

(71) Applicant: CONTEMPORARY AMPEREX TECHNOLOGY (HONG KONG) LIMITED, Hong Kong (CN)

(72) Inventors: Zeli Wu, Ningde (CN); Changlong Han, Ningde (CN); Chenghua Fu, Ningde (CN)

(73) Assignee: CONTEMPORARY AMPEREX TECHNOLOGY (HONG KONG) LIMITED, Hong Kong (CN)

( * ) Notice: Subject to any disclaimer, the term of this patent is extended or adjusted under 35 U.S.C. 154(b) by 340 days.

(21) Appl. No.: 17/506,142

(22) Filed: Oct. 20, 2021

(65) Prior Publication Data

US 2022/0037697 A1    Feb. 3, 2022

Related U.S. Application Data

(63) Continuation of application No. PCT/CN2019/127985, filed on Dec. 24, 2019.

(51) Int. Cl.
| | |
|---|---|
| *H01M 10/0567* | (2010.01) |
| *H01M 4/36* | (2006.01) |
| *H01M 4/38* | (2006.01) |
| *H01M 4/48* | (2010.01) |
| *H01M 4/505* | (2010.01) |
| *H01M 4/525* | (2010.01) |
| *H01M 4/58* | (2010.01) |
| *H01M 4/587* | (2010.01) |
| *H01M 10/0525* | (2010.01) |
| *H01M 10/0569* | (2010.01) |
| *C07D 307/60* | (2006.01) |
| *C07D 309/32* | (2006.01) |
| *C07D 313/04* | (2006.01) |
| *C07F 9/09* | (2006.01) |

(52) U.S. Cl.
CPC ....... *H01M 10/0567* (2013.01); *H01M 4/364* (2013.01); *H01M 4/386* (2013.01); *H01M 4/48* (2013.01); *H01M 4/505* (2013.01); *H01M 4/525* (2013.01); *H01M 4/5825* (2013.01); *H01M 4/587* (2013.01); *H01M 10/0525* (2013.01); *H01M 10/0569* (2013.01); *C07D 307/60* (2013.01); *C07D 309/32* (2013.01); *C07D 313/04* (2013.01); *C07F 9/095* (2013.01); *H01M 2300/0037* (2013.01); *H01M 2300/004* (2013.01)

(58) Field of Classification Search
None
See application file for complete search history.

(56) References Cited

U.S. PATENT DOCUMENTS

2018/0050602 A1    2/2018    Aronov

FOREIGN PATENT DOCUMENTS

| CN | 1523702 A | 8/2004 |
|---|---|---|
| CN | 101657416 A | 2/2010 |
| CN | 101771167 A | 7/2010 |
| CN | 104508896 A | 4/2015 |
| CN | 105917515 A | 8/2016 |
| CN | 108242557 A | 7/2018 |
| CN | 108255315 A | 7/2018 |
| CN | 108598574 A | 9/2018 |
| CN | 109390628 A | 2/2019 |
| CN | 110383565 A | 10/2019 |
| EP | 2675010 A1 | 12/2013 |
| EP | 2849272 A1 | 3/2015 |
| EP | 2882030 A1 | 6/2015 |
| EP | 3096388 A1 | 11/2016 |
| JP | 2013239443 A | 11/2013 |
| KR | 20190141016 A | 12/2019 |
| WO | 2018164124 A1 | 9/2018 |

OTHER PUBLICATIONS

An, F., Zhao, H., Zhou, W. et al. "S-containing and Si-containing compounds as highly effective electrolyte additives for SiOx-based anodes/NCM 811 cathodes in lithium ion cells". Sci Rep 9, 14108 (2019).*
ISR for International Application PCT/CN2019/127985 mailed Sep. 23, 2020.
English Translation for ISR for International Application PCT/CN2019/127985 mailed Sep. 23, 2020.
Written Opinion for International Application PCT/CN2019/127985 mailed Sep. 23, 2020.
First Office Action of CN Application No. 201980098409.2, dated Sep. 12, 2023.
First Examination Report of IN application No. 202217029226, dated Nov. 17, 2022.
First Office Action of JP application No. 2022-520094, dated Mar. 31, 2023.
First Office Action of KR application No. 10-2022-7009816, mailed Jul. 12, 2023.
Decision to grant a patent for EP application No. 19957704.0,dated 20,02.2023.

(Continued)

*Primary Examiner* — Laura Weiner
(74) *Attorney, Agent, or Firm* — Ladas & Parry LLP

(57) ABSTRACT

This application provides a secondary battery and a device comprising the same. The secondary battery includes a negative electrode plate and an electrolyte. The negative electrode plate includes a negative electrode active material. The electrolyte includes an electrolyte salt, an organic solvent, and an additive. The negative electrode active material includes a silicon-based material. The organic solvent includes ethylene carbonate (EC) and diethyl carbonate (DEC). A mass ratio of EC in the organic solvent is less than or equal to 20%, and a mass ratio of DEC in the organic solvent is less than or equal to 20%. The additive includes an additive A and an additive B. The additive A is selected from one or more of compounds represented by Formula 1 or Formula 2, and the additive B is selected from one or more of compounds represented by Formula 3, as described in the application.

14 Claims, 2 Drawing Sheets

(56) References Cited

OTHER PUBLICATIONS

Decision to grant a patent for JP application No. 2022-520094, dated Aug. 7, 2023.
Extended European Search Report of EP Application No. 19957704.0, mailed Feb. 28, 2022, 6 pages.
First Office Action of EP Application No. 19957704.0, mailed Oct. 25, 2022, 5 pages.
Written Opinion of the International Searching Authority on Application No. PCT/CN2019/127985 (English Translation), Sep. 23, 2000, 5 pages.

* cited by examiner

SECONDARY BATTERY AND DEVICE COMPRISING THE SAME

CROSS-REFERENCE TO RELATED APPLICATIONS

This application is a continuation of International Patent Application No. PCT/CN2019/127985 filed on Dec. 24, 2019 the entire content of which is incorporated herein by reference.

TECHNICAL FIELD

This application relates to the technical field of batteries, and in particular, to a secondary battery and a device comprising the same.

BACKGROUND

The increase of depletion of fossil energy and environmental pollution pressure urgently calls for a new type of energy to provide a motive power for the automotive industry. Secondary batteries stand out currently as being a first choice for a motive power supply of new energy vehicles due to a high energy density, no memory effect, and a high operating voltage. However, with the expansion of market demand for electronic products and the development of motive power equipment and energy storage equipment, people are posing higher requirements on the secondary batteries, and it is now urgent to develop a secondary battery of a high energy density.

The use of a silicon-based material of a high specific capacity as a negative electrode active material of the secondary battery can effectively increase the energy density of the secondary battery. However, during charge and discharge cycles, reversible formation and decomposition of a Li—Si alloy lead to sharp deterioration of electrochemical performance of the secondary battery with its size changing by 100% or more.

Therefore, it is urgent to develop a secondary battery of high electrochemical performance without compromising a high energy density.

SUMMARY

In view of problems in background technologies, this application provides a secondary battery and a device comprising the same. The secondary battery achieves good high-temperature cycle performance, good high-temperature storage performance, and a low direct-current internal resistance while keeping a high energy density at the same time.

To achieve the foregoing objective, a first aspect of this application provides a secondary battery. The secondary battery includes a negative electrode plate and an electrolyte. The negative electrode plate includes a negative electrode current collector and a negative electrode film disposed on at least one surface of the negative electrode current collector and comprising a negative electrode active material. The electrolyte includes an electrolyte salt, an organic solvent, and an additive. The negative electrode active material includes a silicon-based material.

The organic solvent includes ethylene carbonate (EC) and diethyl carbonate (DEC). A mass ratio of EC in the organic solvent is less than or equal to 20%, and a mass ratio of DEC in the organic solvent is less than or equal to 20%. The additive includes an additive A and an additive B. The additive A is selected from one or more of compounds represented by Formula 1 or Formula 2:

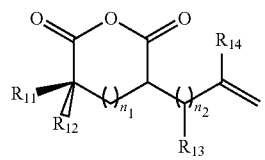

Formula 1

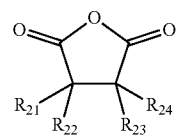

Formula 2 where a value of $n_1$ is 0, 1, 2, 3, 4, or 5; and a value of $n_2$ is 0, 1, 2, 3, 4, 5, 6, 7, 8, or 9; $R_{11}$, $R_{12}$, $R_{13}$, $R_{14}$, $R_{21}$, $R_{22}$, $R_{23}$, and $R_{24}$ are each independently selected from H, F, Cl, Br, I, substituted or unsubstituted C1~C10 chain alkanyls, substituted or unsubstituted C1~C10 chain alkenyls, substituted or unsubstituted C1~C10 chain alkynyls, C1~C10 aliphatic groups, substituted or unsubstituted C3~C9 cyclic alkanyls, substituted or unsubstituted C1~C10 alkoxies, substituted or unsubstituted C6~C20 aryls, or substituted or unsubstituted C3~C20 heteroaryls; and a substituent is selected from one or more of F, Cl, or Br; and the additive B is selected from one or more of compounds represented by Formula 3:

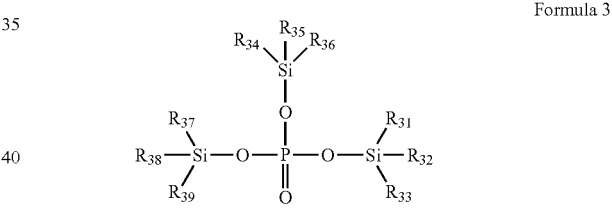

Formula 3 where $R_{31}$, $R_{32}$, $R_{33}$, $R_{34}$, $R_{35}$, $R_{36}$, $R_{37}$, $R_{38}$, $R_{39}$, $R_{41}$, $R_{42}$, $R_{43}$, $R_{44}$, $R_{45}$, $R_{46}$, $R_{47}$, $R_{48}$, and $R_{49}$ are each independently selected from one or more of substituted or unsubstituted C1~C20 alkanyls, substituted or unsubstituted C2~C20 alkenyls, substituted or unsubstituted C2~C20 alkynyls, or substituted or unsubstituted C6~C20 aryls, and a substituent is selected from one or more of F, Cl, or Br.

A Second aspect of this application provides a device, including the secondary battery according to the first aspect of this application.

This application achieves at least the following beneficial effects:

In the secondary battery according to this application, the negative electrode active material includes a silicon-based material, the electrolyte includes a specific type and content of organic solvent, and the additive includes both the additive A and the additive B. Under common action of the solvent and the additive, the secondary battery according to this application achieves good high-temperature cycle performance, good high-temperature storage performance, and a low direct-current resistance at the same time. The device according to this application includes the secondary battery, and therefore, has at least the same advantages as the secondary battery.

Figure 1:
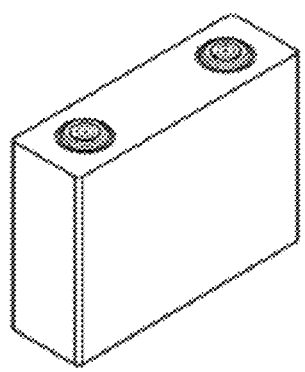
FIG. 1 is a schematic diagram of an implementation of a secondary battery.

Reference numerals are as follows:
1: Battery pack;
2: Upper casing;
3: Lower casing;
4: Battery module; and
5: Secondary battery.

DESCRIPTION OF EMBODIMENTS

The following describes in detail a secondary battery and a device comprising the same according to this application.

A secondary battery is disclosed according to a first aspect of this application. The secondary battery includes a negative electrode plate and an electrolyte. The negative electrode plate includes a negative electrode current collector and a negative electrode film disposed on at least one surface of the negative electrode current collector and comprising a negative electrode active material. The electrolyte includes an electrolyte salt, an organic solvent, and an additive. The negative electrode active material includes a silicon-based material. The organic solvent includes ethylene carbonate (EC) and diethyl carbonate (DEC). A mass ratio of EC in the organic solvent is less than or equal to 20%, and a mass ratio of DEC in the organic solvent is less than or equal to 20%. The additive includes an additive A and an additive B.

In the secondary battery according to the first aspect of this application, the additive A is selected from one or more of compounds represented by Formula 1 or Formula 2. In the formulas, a value of $n_1$ is 0, 1, 2, 3, 4, or 5; and a value of $n_2$ is 0, 1, 2, 3, 4, 5, 6, 7, 8, or 9; $R_{11}$, $R_{12}$, $R_{13}$, $R_{14}$, $R_{21}$, $R_{22}$, $R_{23}$, and $R_{24}$ are each independently selected from H, F, Cl, Br, I, substituted or unsubstituted C1~C10 chain alkanyls, substituted or unsubstituted C1~C10 chain alkenyls, substituted or unsubstituted C1~C10 chain alkynyls, substituted or unsubstituted C3~C9 cyclic alkanyls, substituted or unsubstituted C1~C10 alkoxies, substituted or unsubstituted C6~C20 aryls, or substituted or unsubstituted C3~C20 heteroaryls; and a substituent is selected from one or more of F, Cl, or Br.

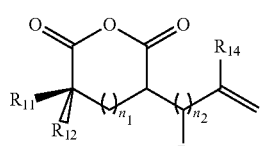

Formula 1

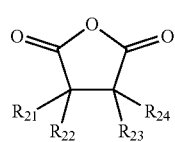

Formula 2

In the secondary battery according to the first aspect of this application, the additive B is selected from one or more of compounds represented by Formula 3, where $R_{31}$, $R_{32}$, $R_{33}$, $R_{34}$, $R_{35}$, $R_{36}$, $R_{37}$, $R_{38}$, $R_{39}$, $R_{41}$, $R_{42}$, $R_{43}$, $R_{44}$, $R_{45}$, $R_{46}$, $R_{47}$, $R_{48}$, and $R_{49}$ are each independently selected from one or more of substituted or unsubstituted C1~C20 alkanyls, substituted or unsubstituted C2~C20 alkenyls, substituted or unsubstituted C2~C20 alkynyls, or substituted or unsubstituted C6~C20 aryls, and a substituent is selected from one or more of F, Cl, or Br.

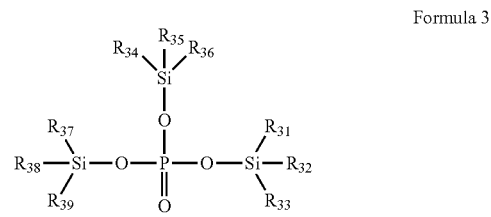

Formula 3

In the secondary battery according to the first aspect of this application, the additive A may be selected from one or more of the following compounds:

Compound A-1

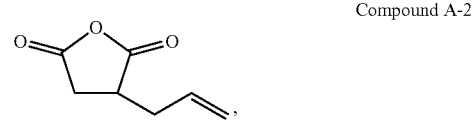

Compound A-2

Compound A-3 and

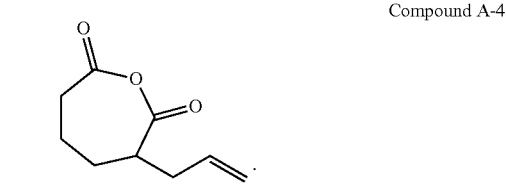

Compound A-4

In the secondary battery according to the first aspect of this application, the additive B may be selected from one or more of the tris(trimethylsilane) phosphate, tris(triethylsilane) phosphate, or tris(vinyldimethylsilane) phosphate; and optionally, the additive B is tris(trimethylsilane) phosphate.

As discovered in a large amount of studies by researchers of this application, when the negative electrode active material of the secondary battery includes a silicon-based material, the organic solvent of the electrolyte contains EC and DEC, the mass ratio of EC in the organic solvent is less than or equal to 20%, the mass ratio DEC in the organic solvent is less than or equal to 20%, and the additive includes the additive A and the additive B, the amount of gas generated by the secondary battery is effectively reduced, and the resistance of the battery is massively decreased, so that secondary battery achieves good high-temperature cycle performance, good high-temperature storage performance, and a low direct-current resistance at the same time.

In the secondary battery according to the first aspect of this application, optionally, the mass ratio of EC in the organic solvent is 10%~20%. With the content of EC falling within such a range, the high-temperature cycle performance of the battery is further improved.

In the secondary battery according to the first aspect of this application, optionally, the mass ratio of DEC in the organic solvent is 10%~20%. With the content of DEC falling within such a range, the amount of gas generated by the secondary battery is further reduced, and the high-temperature storage performance of the battery is improved.

In the secondary battery according to the first aspect of this application, optionally, the mass ratio of the additive A in the electrolyte is less than or equal to 1%. When the content of the additive A is within the given range, the high-temperature cycle performance and the high-temperature storage performance of the battery are improved effectively. When the content of the additive A is too high, the additive A will form, on surfaces of positive and negative electrodes, a passivation film whose resistance increases significantly, and also affect the high-temperature storage performance of the battery. Optionally, the mass ratio of the additive A in the electrolyte is 0.1%~0.5%.

In the secondary battery according to the first aspect of this application, optionally, the mass ratio of the additive B in the electrolyte is less than or equal to 2%. When the content of the additive B is within the given range, the resistance of the battery is reduced effectively. When the content of the additive B is too high, the additive B will generate a considerable amount of $LiPO_3$ and $(CH_3)_3SiF$ on the surface of the negative electrode, and thus affect the high-temperature storage performance of the secondary battery. Optionally, the mass ratio of the additive B in the electrolyte is 0.1%~1%.

In the secondary battery according to the first aspect of this application, optionally, the organic solvent further includes ethyl methyl carbonate (EMC). A mass ratio of EMC in the organic solvent is greater than 50%. Optionally, the mass ratio of EMC in the organic solvent is 55%~65%.

In the secondary battery according to the first aspect of this application, optionally, the additive further includes fluoroethylene carbonate (FEC). A mass ratio of FEC in the electrolyte is less than or equal to 8%. Optionally, the mass ratio of FEC in the electrolyte is 5%~8%.

In the secondary battery according to the first aspect of this application, optionally, the additive further includes one or more of ethylene sulfate (DTD), 1,3-propane sultone (PS), 1,3-propene sultone (PST), lithium difluorooxalate borate (LiDFOB), or lithium difluorobisoxalate phosphate (LiDFOP).

In the secondary battery according to the first aspect of this application, optionally, the electrolyte salt includes one or more of lithium hexafluorophosphate, lithium bis(fluorosulfonyl)imide, lithium tetrafluoroborate, or lithium perchlorate. Optionally, the electrolyte salt includes one or more of lithium hexafluorophosphate or lithium bis(fluorosulfonyl)imide.

In the secondary battery according to the first aspect of this application, optionally, a concentration of the electrolyte salt in the electrolyte is 1.0 mol/L~1.3 mol/L, optionally 1.0 mol/L~1.2 mol/L.

In the secondary battery according to the first aspect of this application, optionally, a conductivity of the electrolyte at 25° C. is 7 mS/cm~9.5 mS/cm. Optionally, the conductivity of the electrolyte at 25° C. is 7 mS/cm~8.5 mS/cm.

In the secondary battery according to the first aspect of this application, optionally, a viscosity of the electrolyte at 25° C. is 3 mPa·s~4.5 mPa·s. Optionally, the viscosity of the electrolyte at 25° C. is 3 mPa·s~3.5 mPa·s.

The conductivity of the electrolyte at 25° C. may be measured by a known method in the art, and may be measured by using a Leici conductivity meter.

The viscosity of the electrolyte at 25° C. may be measured by a known method in the art, and may be measured by using a viscometer.

In the secondary battery according to the first aspect of this application, the silicon-based material includes one or more of elemental silicon, a silicon-carbon composite, a silicon-oxygen compound, a silicon-nitrogen compound, or a silicon alloy. Optionally, the silicon-based material includes a silicon-oxygen compound.

In the secondary battery according to the first aspect of this application, optionally, the negative electrode active material further includes a carbon material. The carbon material includes one or more of natural graphite, artificial graphite, soft carbon, or hard carbon. Optionally, the carbon material includes one or more of natural graphite or artificial graphite.

In the secondary battery according to the first aspect of this application, the type of the negative electrode current collector is not limited, and may be selected according to actual needs. Specifically, the negative electrode current collector may be a metal foil such as a copper foil.

In the secondary battery according to the first aspect of this application, the secondary battery further includes a positive electrode plate. The positive electrode plate includes a positive electrode current collector and a positive electrode film disposed on at least one surface of the positive electrode current collector and comprising a positive electrode active material.

In the secondary battery according to the first aspect of this application, optionally, the positive electrode active material includes one or more of a lithium nickel cobalt manganese oxide or a lithium nickel cobalt aluminum oxide. The lithium nickel cobalt manganese oxide and the lithium nickel cobalt aluminum oxide serving as positive electrode active materials of the secondary battery have the advantages of a high specific capacity and a long cycle life, and further improve electrochemical performance of the battery when used together with the negative electrode active material that includes a silicon-based material.

In the secondary battery according to the first aspect of this application, optionally, the positive electrode active material includes one or more of $Li_aNi_bCo_cM_dM'_eO_fA_g$ or $Li_aNi_bCo_cM_dM'_eO_fA_g$ with a coating layer coated on at least a part of the surface of the $Li_aNi_bCo_cM_dM'_eO_fA_g$, where 0.8≤a≤1.2, 0.5≤b<1, 0<c<1, 0<d<1, 0≤e≤0.1, 1≤f≤2, and 0≤g≤1; M is one or more of Mn or Al; M' is selected from one or more of Zr, Al, Zn, Cu, Cr, Mg, Fe, V, Ti, or B; and A is selected from one or more of N, F, S, or Cl.

A coating layer of the positive electrode active material may be a carbon layer, an oxide layer, an inorganic salt layer, or a conductive polymer layer. The cycle performance of the secondary battery can be further improved by surface modification on the coating of the positive electrode active material.

In the secondary battery according to the first aspect of this application, optionally, the positive electrode active material may include one or more of a lithium nickel oxide (such as a lithium nickel oxide), a lithium manganese oxide (such as a spinel-type lithium manganate oxide or a laminated lithium manganate oxide), a lithium iron phosphate, a lithium manganese phosphate, a lithium cobalt oxide, or a doped/coated modified compound thereof.

In the secondary battery according to the first aspect of this application, the type of the positive electrode current collector is not limited, and may be selected according to actual needs. Specifically, the positive electrode current collector may be a metal foil such as an aluminum foil.

In the secondary battery according to the first aspect of this application, the secondary battery further includes a separator. The type of the separator is not limited, and may be selected according to actual needs. Specifically, the separator may be selected from a polyethylene film, a polypropylene film, a polyvinylidene fluoride film, or a multilayer composite film thereof.

In some embodiments, the secondary battery may include an outer package configured to package the positive electrode plate, the negative electrode plate, and the electrolyte. For example, the positive electrode plate, the negative electrode plate, and the separator may be laminated to form a laminated electrode assembly or may be wound to form a wound electrode assembly. The electrode assembly is packaged in an outer package, and the electrolyte infiltrates the electrode assembly. The quantity of electrode assemblies in the secondary battery may be one or more, and is adjustable according to needs.

In some embodiments, the outer package of the secondary battery may be a soft package such as a pouch-type soft package. The material of the soft package may be plastic such as one or more of polypropylene (PP), polybutylene terephthalate (PBT), or polybutylene succinate (PBS). The outer package of the secondary battery may also be a hard casing such as an aluminum casing.

The shape of the secondary battery is not limited in this application, and may be cylindrical, prismatic or of any other shape. FIG. 1 shows a prismatic secondary battery 5 as an example.

In some embodiments, the secondary battery may be assembled into a battery module. The battery module may contain a plurality of secondary batteries, and the specific quantity of the secondary batteries in a battery module may be adjusted according to the application and capacity of the battery module.

Figure 2:
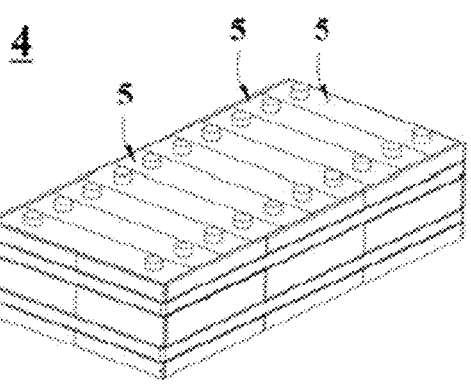
FIG. 2 is a schematic diagram of an implementation of a battery module.

FIG. 2 shows a battery module 4 as an example. Referring to FIG. 2, in the battery module 4, a plurality of secondary batteries 5 may be arranged sequentially along a length direction of the battery module 4. Nevertheless, the secondary batteries may also be arranged in any other manner. Further, the plurality of secondary batteries 5 may be fixed by fasteners.

Optionally, the battery module 4 may further include a housing that provides an accommodation space. A plurality of secondary batteries 5 are accommodated in the accommodation space.

In some embodiments, the battery module may be assembled into a battery pack. The quantity of the battery modules contained in a battery pack may be adjusted according to the application and capacity of the battery pack.

Figure 3:
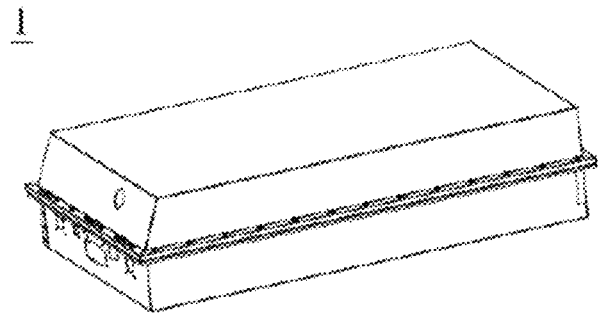
FIG. 3 is a schematic diagram of an implementation of a battery pack.
Figure 4:
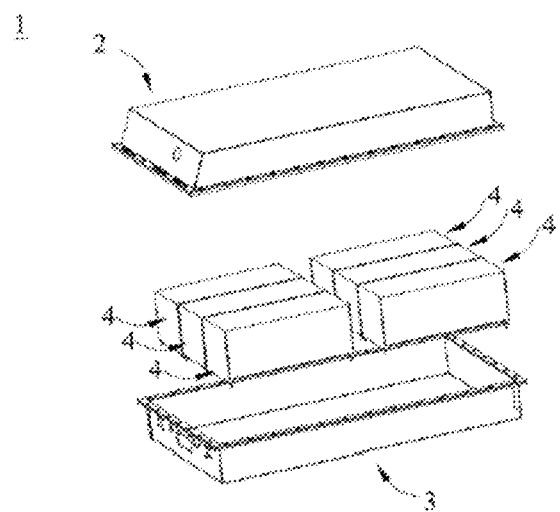
FIG. 4 is an exploded view of FIG. 3.

FIG. 3 and FIG. 4 shows a battery pack 1 as an example. Referring to FIG. 3 and FIG. 4, the battery pack 1 may include a battery casing and a plurality of battery modules 4 contained in the battery casing. The battery casing includes an upper casing 2 and a lower casing 3. The upper casing 2 engages with the lower casing 3 to form a closed space for accommodating the battery module 4. The plurality of battery modules 4 may be arranged in the battery casing in any manner.

A second aspect of this application provides a device, including the secondary battery according to the first aspect of this application. The secondary battery may be used as a power supply to the device, or as an energy storage unit of the device. The device includes, but is not limited to, a mobile device (such as a mobile phone or a laptop computer), an electric vehicle (such as a battery electric vehicle, a hybrid electric vehicle, a plug-in hybrid electric vehicle, an electric bicycle, an electric scooter, an electric golf cart, or an electric truck), an electric train, a ship, a satellite system, or an energy storage system.

A secondary battery, a battery module, or a battery pack may be selected for the device according to use requirements of the device.

Figure 5:
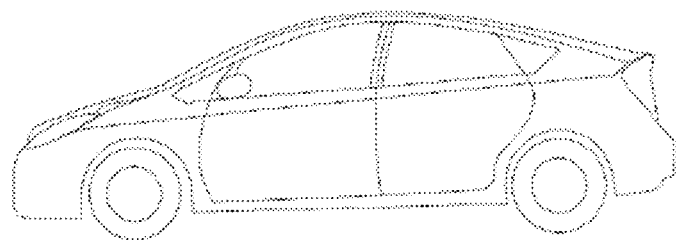
FIG. 5 is a schematic diagram of an implementation of a device using a secondary battery as a power supply.

FIG. 5 shows a device as an example. The device may be battery electric vehicle, a hybrid electric vehicle, a plug-in hybrid electric vehicle, or the like. To meet the requirements of the device for a high power and a high energy density of the secondary battery, a battery pack or a battery module may be adopted.

The device used as another example may be a mobile phone, a tablet computer, a notebook computer, or the like. The device is generally required to be thin and light, and may have a secondary battery as a power supply.

This application is further described below with reference to embodiments. Understandably, the embodiments are only intended to illustrate this application but not to limit the scope of this application.

The secondary batteries in Embodiments 1~31 and Comparative Embodiments 1~5 are prepared using the following method:

(1) Preparing a Positive Electrode Plate

Mixing a positive electrode active material ($LiNi_{0.8}Co_{0.1}Mn_{0.1}O_2$), a conductive agent (Super P), and a binder (polyvinylidene difluoride) at a weight ratio of 98:1:1, and then adding an N-methyl-pyrrolidone solvent system; stirring the mixture with a vacuum mixer until the system becomes homogeneous and transparent so that a positive electrode slurry is obtained; coating an aluminum foil of a positive electrode current collector with the positive electrode slurry homogeneously; drying the aluminum foil in the air under a room temperature, and moving the aluminum foil into an oven for drying, and then performing cold calendering and slitting to obtain a positive electrode plate.

(2) Preparing a Negative Electrode Plate

Mixing a negative electrode active material (silicon suboxide) and artificial graphite at a mass ratio of 2:8, then mixing the mixture with a conductive agent (Super P), a thickener (sodium carboxymethyl cellulose (CMC-Na)), and a binder (styrene butadiene rubber (SBR)) at a mass ratio of 92:2:2:4, and then adding deionized water; stirring the mixture with a vacuum mixer to obtain a negative electrode slurry; coating a copper foil of the negative electrode current collector with the negative electrode slurry homogeneously; drying the copper foil in the air under a room temperature, and then moving the copper foil into an oven for drying, and then performing cold calendering and slitting to obtain a negative electrode plate.

(3) Preparing an Electrolyte

Preparing a mixed organic solvent in an argon atmosphere glovebox with a water content of less than 10 ppm, then dissolving a fully dried electrolyte salt in the mixed organic solvent, adding an additive, and then mixing them homogeneously to obtain an electrolyte. Specific types and content of the organic solvents and additives used in the electrolyte are shown in Table 1. In Table 1, each organic solvent is a mass ratio calculated based on a total mass of the organic solvent, and the content of each additive is a mass ratio calculated based on a total mass of the electrolyte.

(4) Preparing a Separator

Using a polyethylene film as a separator.

(5) Preparing a Secondary Battery

Sequentially stacking the positive electrode plate, the separator, and the negative electrode plate so that the separator is located between the positive electrode plate and the negative electrode plate for a purpose of separation, and then winding them to obtain an electrode assembly; placing the electrode assembly in an outer package, and injecting the electrolyte prepared above into the battery which has been dried; and performing steps such as vacuum packaging, standing, formation, and reshaping to obtain a secondary battery.

TABLE 1

Parameters in Embodiments 1~31 and Comparative Embodiments 1~5

| | Electrolyte | | | | | | | |
|---|---|---|---|---|---|---|---|---|
| | Solvent | Electrolyte salt Type | Additive A | | Additive B | | Other additives | |
| Serial number | Type and mass ratio | and concentration | Type | Content (%) | Type | Content (%) | Type | Content (%) |
| Embodiment 1 | EC:EMC:DEC = 20%:60%:20% | LiPF$_6$: 1.3 mol/L | Compound A-1 | 0.05% | Tris(tri-methylsilane) phosphate | 0.5% | FEC | 8% |
| Embodiment 2 | EC:EMC:DEC = 20%:60%:20% | LiPF$_6$: 1.3 mol/L | Compound A-1 | 0.1% | Tris(tri-methylsilane) phosphate | 0.5% | FEC | 8% |
| Embodiment 3 | EC:EMC:DEC = 20%:60%:20% | LiPF$_6$: 1.3 mol/L | Compound A-1 | 0.2% | Tris(tri-methylsilane) phosphate | 0.5% | FEC | 8% |
| Embodiment 4 | EC:EMC:DEC = 20%:60%:20% | LiPF$_6$: 1.3 mol/L | Compound A-1 | 0.5% | Tris(tri-methylsilane) phosphate | 0.5% | FEC | 8% |
| Embodiment 5 | EC:EMC:DEC = 20%:60%:20% | LiPF$_6$: 1.3 mol/L | Compound A-1 | 1.0% | Tris(tri-methylsilane) phosphate | 0.5% | FEC | 8% |
| Embodiment 6 | EC:EMC:DEC = 20%:60%:20% | LiPF$_6$: 1.3 mol/L | Compound A-1 | 1.5% | Tris(tri-methylsilane) phosphate | 0.5% | FEC | 8% |
| Embodiment 7 | EC:EMC:DEC = 20%:60%:20% | LiPF$_6$: 1.3 mol/L | Compound A-1 | 0.5% | Tris(tri-methylsilane) phosphate | 0.05% | FEC | 8% |
| Embodiment 8 | EC:EMC:DEC = 20%:60%:20% | LiPF$_6$: 1.3 mol/L | Compound A-1 | 0.5% | Tris(tri-methylsilane) phosphate | 0.1% | FEC | 8% |
| Embodiment 9 | EC:EMC:DEC = 20%:60%:20% | LiPF$_6$: 1.3 mol/L | Compound A-1 | 0.2% | Tris(tri-methylsilane) phosphate | 0.3% | FEC | 8% |
| Embodiment 10 | EC:EMC:DEC = 20%:60%:20% | LiPF$_6$: 1.3 mol/L | Compound A-1 | 0.5% | Tris(tri-methylsilane) phosphate | 0.8% | FEC | 8% |
| Embodiment 11 | EC:EMC:DEC = 20%:60%:20% | LiPF$_6$: 1.3 mol/L | Compound A-1 | 0.5% | Tris(tri-methylsilane) phosphate | 1% | FEC | 8% |
| Embodiment 12 | EC:EMC:DEC = 20%:60%:20% | LiPF$_6$: 1.3 mol/L | Compound A-1 | 0.2% | Tris(tri-methylsilane) phosphate | 1.5% | FEC | 8% |
| Embodiment 13 | EC:EMC:DEC = 20%:60%:20% | LiPF$_6$: 1.3 mol/L | Compound A-1 | 0.5% | Tris(tri-methylsilane) phosphate | 2.5% | FEC | 8% |
| Embodiment 14 | EC:EMC:DEC = 15%:65%:20% | LiPF$_6$: 1.3 mol/L | Compound A-1 | 0.5% | Tris(tri-methylsilane) phosphate | 0.5% | FEC | 8% |
| Embodiment 15 | EC:EMC:DEC = 10%:70%:20% | LiPF$_6$: 1.3 mol/L | Compound A-1 | 0.5% | Tris(tri-methylsilane) phosphate | 0.5% | FEC | 8% |
| Embodiment 16 | EC:EMC:DEC = 20%:65%:15% | LiPF$_6$: 1.3 mol/L | Compound A-1 | 0.5% | Tris(tri-methylsilane) phosphate | 0.5% | FEC | 8% |
| Embodiment 17 | EC:EMC:DEC = 20%:70%:10% | LiPF$_6$: 1.3 mol/L | Compound A-1 | 0.5% | Tris(tri-methylsilane) phosphate | 0.5% | FEC | 8% |
| Embodiment 18 | EC:EMC:DEC = 20%:60%:20% | LiPF$_6$: 1.3 mol/L | Compound A-2 | 0.5% | Tris(tri-methylsilane) phosphate | 0.5% | FEC | 8% |
| Embodiment 19 | EC:EMC:DEC = 20%:60%:20% | LiPF$_6$: 1.3 mol/L | Compound A-3 | 0.5% | Tris(tri-methylsilane) phosphate | 0.5% | FEC | 8% |

TABLE 1-continued

Parameters in Embodiments 1~31 and Comparative Embodiments 1~5

| | | Electrolyte | | | | | | |
|---|---|---|---|---|---|---|---|---|
| | Solvent | Electrolyte salt Type | Additive A | | Additive B | | Other additives | |
| Serial number | Type and mass ratio | and concentration | Type | Content (%) | Type | Content (%) | Type | Content (%) |
| Embodiment 20 | EC:EMC:DEC = 20%:60%:20% | LiPF$_6$: 1.3 mol/L | Compound A-1/ compound A-2 | 0.25% + 0.25% | Tris(tri-methylsilane) phosphate | 0.5% | FEC | 8% |
| Embodiment 21 | EC:EMC:DEC = 20%:60%:20% | LiPF$_6$: 1.3 mol/L | Compound A-1 | 0.5% | Tris(tri-methylsilane) phosphate | 0.5% | FEC | 8% |
| Embodiment 22 | EC:EMC:DEC = 20%:60%:20% | LiPF$_6$: 1.3 mol/L | Compound A-1 | 0.5% | Tris(tri-methylsilane) phosphate | 0.5% | FEC | 8% |
| Embodiment 23 | EC:EMC:DEC = 20%:60%:20% | LiPF$_6$: 1 mol/L | Compound A-1 | 0.5% | Tris(tri-methylsilane) phosphate | 0.5% | FEC | 8% |
| Embodiment 24 | EC:EMC:DEC = 20%:60%:20% | LiPF$_6$: 1 mol/L | Compound A-1 | 0.5% | Tris(tri-methylsilane) phosphate | 0.5% | FEC | 8% |
| Embodiment 25 | EC:EMC:DEC = 20%:60%:20% | LiPF$_6$: 1.2 mol/L | Compound A-1 | 0.5% | Tris(tri-methylsilane) phosphate | 0.5% | FEC | 8% |
| Embodiment 26 | EC:EMC:DEC = 5%:75%:20% | LiPF$_6$: 1.3 mol/L | Compound A-1 | 0.5% | Tris(tri-methylsilane) phosphate | 0.5% | FEC | 8% |
| Embodiment 27 | EC:EMC:DEC = 20%:75%:5% | LiPF$_6$: 1.3 mol/L | Compound A-1 | 0.5% | Tris(tri-methylsilane) phosphate | 0.5% | FEC | 8% |
| Embodiment 28 | EC:EMC:DEC = 20%:60%:20% | LiPF$_6$: 1.3 mol/L | Compound A-1 | 0.5% | Tris(tri-methylsilane) phosphate | 0.5% | FEC | 8% |
| Embodiment 29 | EC:EMC:DEC = 20%:60%:20% | LiPF$_6$: 1.3 mol/L | Compound A-1 | 0.5% | Tris(tri-methylsilane) phosphate | 0.5% | FEC | 4% |
| Embodiment 30 | EC:EMC:DEC = 20%:60%:20% | LiPF$_6$: 1.3 mol/L | Compound A-1 | 0.5% | Tris(tri-methylsilane) phosphate | 0.5% | FEC | 6% |
| Embodiment 31 | EC:EMC:DEC = 20%:60%:20% | LiPF$_6$: 1.3 mol/L | Compound A-1 | 0.5% | Tris(tri-methylsilane) phosphate | 0.5% | FEC | 10% |
| Comparative Embodiment 1 | EC:EMC:DEC = 20%:60%:20% | LiPF$_6$: 1.3 mol/L | Compound A-1 | 0.5% | / | / | FEC | 8% |
| Comparative Embodiment 2 | EC:EMC:DEC = 20%:60%:20% | LiPF$_6$: 1.3 mol/L | / | / | Tris(tri-methylsilane) phosphate | 0.5% | FEC | 8% |
| Comparative Embodiment 3 | EC:EMC:DEC = 30%:50%:20% | LiPF$_6$: 1.3 mol/L | Compound A-1 | 0.5% | Tris(tri-methylsilane) phosphate | 0.5% | FEC | 8% |
| Comparative Embodiment 4 | EC:EMC:DEC = 20%:50%:30% | LiPF$_6$: 1.3 mol/L | Compound A-1 | 0.5% | Tris(tri-methylsilane) phosphate | 0.5% | FEC | 8% |
| Comparative Embodiment 5 | EC:EMC:DEC = 20%:60%:20% | LiPF$_6$: 1.3 mol/L | Compound A-1 | 0.5% | Tris(tri-methylsilane) borate | 0.5% | FEC | 8% |

The following describes a test process of the secondary battery.

(1) Testing High-Temperature Storage Performance

Charging the secondary battery under 25° C. at a constant current rate of 0.5C until the voltage reaches 4.25 V, and then charging the battery at a constant voltage of 4.2 V until the current drops to 0.05C; measuring the volume of the secondary battery at this time by using a drainage method, and recording a result as V0; putting the secondary battery into an 60° C. thermostat, keeping it stored for 30 days, and then taking it out; and measuring the volume of the secondary battery at this time, and recording a result as V2.

Volume expansion rate of the secondary battery after storage under 60° C. for 30 days (%)=[(V2−V1)/V1]×100%.

(2) Testing High-Temperature Cycle Performance

Charging the secondary battery under 45° C. at a constant current rate of 1C until the voltage reaches 4.25 V, then charging the battery at a constant voltage of 4.25 V until the current drops to 0.05C, and leaving the battery to stand for 5 minutes; and then discharging the battery to 2.5 V at a constant current rate of 1C, thereby completing a first-cycle charge/discharge process of the secondary battery, where a discharge capacity at the end of the first cycle is a first-cycle discharge capacity of the secondary battery; performing 800 cycles of charge/discharge of the secondary battery according to the foregoing process, and recording a discharge capacity of the secondary battery after 800 cycles.

Capacity retention rate (%) of the secondary battery after 800 cycles under 45° C.=discharge capacity of the secondary battery after 800 cycles/discharge capacity of the secondary battery after the first cycle×100%.

(3) Testing a Direct-Current Resistance

Charging the secondary battery under 25° C. to a 50% state of charge (SOC) by using a 0.5C constant current rate/constant voltage, and leaving the battery to stand 10 minutes; discharging the battery for 10 seconds at a constant current rate ($I_1$) of 0.1C, and recording a voltage $U_1$ of the discharged secondary battery; and discharging the secondary battery for 30 seconds at a constant current rate ($I_2$) of 4C, and recording a voltage $U_2$ of the discharged secondary battery.

Direct-current resistance of the secondary battery DCR= $(U_1-U_2)/(I_2-I_1)$.

TABLE 2

Performance Test Results of Embodiments 1~31 and Comparative Embodiments 1~5

| Serial number | Volume expansion rate (%) after storing for 30 days under 60° C. | Capacity retention rate (%) after 800 cycles under 45° C. | DCR/mohm |
|---|---|---|---|
| Embodiment 1 | 25.1 | 84.9 | 27.1 |
| Embodiment 2 | 23.4 | 86.1 | 28.8 |
| Embodiment 3 | 22.9 | 88.5 | 29.7 |
| Embodiment 4 | 19.2 | 90.1 | 31.0 |
| Embodiment 5 | 24.1 | 88.1 | 34.0 |
| Embodiment 6 | 28.9 | 83.1 | 37.0 |
| Embodiment 7 | 20.7 | 85.6 | 38.1 |
| Embodiment 8 | 20.1 | 87.8 | 36.9 |
| Embodiment 9 | 19.7 | 88.1 | 35.1 |
| Embodiment 10 | 22.9 | 87.1 | 29.7 |
| Embodiment 11 | 21.9 | 86.0 | 28.0 |
| Embodiment 12 | 23.9 | 85.0 | 27.2 |
| Embodiment 13 | 33.8 | 83.0 | 25.1 |
| Embodiment 14 | 18.1 | 89.9 | 32.5 |
| Embodiment 15 | 16.7 | 87.5 | 33.0 |
| Embodiment 16 | 20.6 | 86.8 | 29.7 |
| Embodiment 17 | 21.6 | 86.1 | 28.6 |
| Embodiment 18 | 25.8 | 84.6 | 30.5 |
| Embodiment 19 | 27.9 | 85.1 | 28.6 |
| Embodiment 20 | 27.5 | 86.1 | 27.6 |
| Embodiment 21 | 32.7 | 83.5 | 29.1 |
| Embodiment 22 | 34.5 | 83.1 | 30.7 |
| Embodiment 23 | 17.9 | 87.4 | 27.6 |
| Embodiment 24 | 18.1 | 88.0 | 28.6 |
| Embodiment 25 | 17.4 | 91.2 | 33.1 |
| Embodiment 26 | 15.1 | 90.5 | 36.1 |
| Embodiment 27 | 16.9 | 87.1 | 31.9 |
| Embodiment 28 | 20.1 | 92.1 | 31.5 |
| Embodiment 29 | 15.1 | 86.1 | 26.1 |
| Embodiment 30 | 17.1 | 88.6 | 28.9 |
| Embodiment 31 | 23.5 | 88.8 | 34.1 |
| Comparative Embodiment 1 | 21.4 | 83.0 | 51.7 |
| Comparative Embodiment 2 | 39.9 | 77.8 | 37.0 |
| Comparative Embodiment 3 | 39.7 | 82.1 | 38.6 |
| Comparative Embodiment 4 | 18.1 | 76.9 | 35.1 |
| Comparative Embodiment 5 | 35.7 | 82.5 | 40.1 |

As can be learned from the test results in Table 2, the organic solvent in the electrolyte according to Embodiments 1~31 of this application contains EC and DEC. The mass ratio of EC in the organic solvent and the mass ratio DEC in the organic solvent are not higher than 20%, and the additive includes both the additive A and the additive B. Under common action of such organic solvent and additives, the secondary battery according to this application achieves good high-temperature cycle performance, good high-temperature storage performance, and a low direct-current resistance at the same time.

By contrast, in Embodiment 1, only the additive A is added into the electrolyte. Although the high-temperature storage performance and the high-temperature cycle performance of the battery are improved, the direct-current internal resistance of the battery increases.

In Comparative Embodiment 2, only the additive B is added into the electrolyte. Although the direct-current internal resistance of the battery is relatively improved, the use of the additive B alone increases the content of $(CH_3)_3SiF$ and $LiPOF_3$ in the secondary battery, thereby deteriorating the high-temperature storage performance and the high-temperature cycle performance of the battery.

In Embodiment 3, the mass ratio of EC of the electrolyte in the organic solvent is greater than 20%, thereby deteriorating the high-temperature storage performance of the battery.

In Embodiment 4, the mass ratio of DEC of the electrolyte in the organic solvent is greater than 20%, thereby deteriorating the high-temperature cycle performance of the battery.

In Embodiment 5, the additive B in the electrolyte is tris(trimethylsilane)borate, resulting in inferior overall performance of the battery.

In conclusion, under common action of the organic solvent and the additive, the electrolyte according to this application enables the secondary battery to achieve good high-temperature cycle performance, good high-temperature storage performance, and a low direct-current resistance at the same time.

What is claimed is:

1. A secondary battery comprising a positive electrode plate, a negative electrode plate and an electrolyte, wherein the negative electrode plate comprises a negative electrode current collector and a negative electrode film disposed on at least one surface of the negative electrode current collector and comprising a negative electrode active material, and the electrolyte comprises an electrolyte salt, an organic solvent, and an additive, wherein the negative electrode active material comprises a silicon-based material;

the organic solvent comprises ethylene carbonate (EC), diethyl carbonate (DEC) and ethyl methyl carbonate (EMC), a mass ratio of EC in the organic solvent is 5% to 20%, a mass ratio of DEC in the organic solvent is 5% to 20%, and a mass ratio of EMC in the organic solvent is 55%-65%;

the additive comprises an additive A and an additive B; and the additive A is selected from one or more of compounds represented by Formula 2:

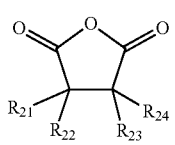

Formula 2 wherein
R$_{21}$, R$_{22}$, R$_{23}$, and R$_{24}$ are each independently selected from the group consisting of H, F, Cl, Br, I, substituted or unsubstituted C1-C10 chain alkyls, substituted or unsubstituted C1-C10 chain alkenyls, substituted or unsubstituted C1-C10 chain alkynyls, C1-C10 aliphatic groups, substituted or unsubstituted C3-C9 cyclic alkyls, substituted or unsubstituted C1-C10 alkoxys, substituted or unsubstituted C6-C20 aryls, and substituted or unsubstituted C3-C20 heteroaryls; and the substituent is selected from one or more of the group consisting of F, Cl, and Br; and the additive B is selected from one or more of compounds-represented by Formula 3:

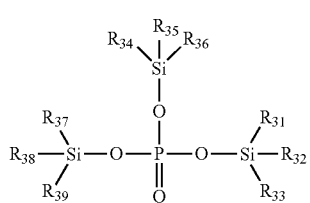

Formula 3 wherein R$_{31}$, R$_{32}$, R$_{33}$, R$_{34}$, R$_{35}$, R$_{36}$, R$_{37}$, R$_{38}$ and R$_{39}$ are independently selected from one or more the group consisting of substituted or unsubstituted C1-C20 alkyls, substituted or unsubstituted C2-C20 alkenyls, substituted or unsubstituted C2-C20 alkynyls, and] substituted or unsubstituted C6-C20 aryls, and a substituent selected from one or more of the group consisting of F, Cl, and Br;

wherein a mass ratio of the additive A in the electrolyte is equal to or greater than 0.05% to less than or equal to 1%;
wherein a mass ratio of the additive B in the electrolyte is equal to or greater than 0.1% to less than or equal to 2%;
wherein the positive electrode plate comprises a positive electrode current collector and a positive electrode film disposed on at least one surface of the positive electrode current collector, and
wherein the positive electrode film comprises a positive electrode active material, and the positive electrode active material comprises a lithium nickel cobalt manganese oxide.

2. The secondary battery according to claim 1, wherein the mass ratio of EC in the organic solvent is 10%-20%.

3. The secondary battery according to claim 1, wherein the mass ratio of DEC in the organic solvent is 10%-20%.

4. The secondary battery according to claim 1, wherein the additive A is the following compound:

Compound A-1

5. The secondary battery according to claim 1, wherein the additive B is tris(trimethylsilane) phosphate.

6. The secondary battery according to claim 1, wherein the additive further comprises fluoroethylene carbonate (FEC), and a mass ratio of FEC in the electrolyte is 5% to 8%.

7. The secondary battery according to claim 1, wherein the additive further comprises one or more of ethylene sulfate (DTD), 1,3-propane sultone (PS), 1,3-propene sultone (PST), lithium difluorooxalate borate (LiDFOB), or lithium difluorobisoxalate phosphate (LiDFOP).

8. The secondary battery according to claim 1, wherein: a conductivity of the electrolyte at 25° C. is 7 mS/cm-9.5 mS/cm.

9. The secondary battery according to claim 1, wherein the silicon-based material comprises a silicon-oxygen compound.

10. The secondary battery according to claim 1, wherein the negative electrode active material further comprises a carbon material, and the carbon material comprises one or more of natural graphite or artificial graphite.

11. The secondary battery according to claim 1, wherein the positive electrode active material further comprises a lithium iron phosphate.

12. A device, comprising the secondary battery according to claim 1.

13. The secondary battery according to claim 1, wherein a viscosity of the electrolyte at 25° C. is 3 mPa·s-4.5 mPa·s.

14. The secondary battery according to claim 1, wherein a concentration of the electrolyte salt in the electrolyte is 1.0 mol/L-1.3 mol/L.

* * * * *